US010178355B2

(12) United States Patent
Voyer et al.

(10) Patent No.: US 10,178,355 B2
(45) Date of Patent: Jan. 8, 2019

(54) TRACKING SYSTEM AND METHOD FOR TRACKING WOOD PRODUCTS IN A PRODUCTION LINE

(71) Applicant: VAB SOLUTIONS INC., Lévis (CA)

(72) Inventors: Marc Voyer, Québec (CA); Marc-Antoine Paquet, Lévis (CA)

(73) Assignee: VAB SOLUTIONS INC., Lévis (CA)

( * ) Notice: Subject to any disclaimer, the term of this patent is extended or adjusted under 35 U.S.C. 154(b) by 0 days.

(21) Appl. No.: 15/446,082

(22) Filed: Mar. 1, 2017

(65) Prior Publication Data

US 2017/0257603 A1    Sep. 7, 2017

Related U.S. Application Data

(60) Provisional application No. 62/301,797, filed on Mar. 1, 2016.

(51) Int. Cl.
*H04N 7/18* (2006.01)
*G06T 7/70* (2017.01)
(Continued)

(52) U.S. Cl.
CPC ......... *H04N 7/183* (2013.01); *G01N 21/8986* (2013.01); *G06Q 10/087* (2013.01);
(Continued)

(58) Field of Classification Search
CPC ......... H04N 7/183; G06T 7/70; G06T 7/0004; G06T 2207/30161; G01N 21/8986; G06Q 10/087

See application file for complete search history.

(56) References Cited

U.S. PATENT DOCUMENTS 4,596,172 A * 6/1986 Visser .................. B23D 47/042
83/210
6,466,305 B1 * 10/2002 McBain ................. G01B 11/00
250/559.25
(Continued)

FOREIGN PATENT DOCUMENTS

CA        2245412 A1    2/2000
CA        2533516 A1    2/2005
(Continued)

*Primary Examiner* — Oleg Asanbayev
(74) *Attorney, Agent, or Firm* — Norton Rose Fulbright Canada LLP; Alexandre Daoust

(57) ABSTRACT

The wood tracking system for a production line generally has a wood product optimizer; a wood product trimmer downstream from the optimizer in the production line; a conveyor for moving wood products from the optimizer to the trimmer and across a handling area therebetween, the optimizer being configured to scan each of the wood products in a given order and to generate optimization data for each wood product; and a computer vision system positioned proximate the handling area along the production line, the computer vision system having a camera, a processor in communication with the optimizer and with the trimmer and a computer-readable memory for storing the optimization data, the processor being configured to acquire images of the handling area from the camera, the processor being configured to associate the optimization data of a given wood product across each of the images until it arrives at the trimmer.

5 Claims, 5 Drawing Sheets

(51) Int. Cl.
*G06T 7/00* (2017.01)
*G01N 21/898* (2006.01)
*G06Q 10/08* (2012.01)

(52) U.S. Cl.
CPC .............. G06T 7/0004 (2013.01); G06T 7/70 (2017.01); *G06T 2207/30161* (2013.01)

(56) References Cited

U.S. PATENT DOCUMENTS

| | | | | |
|---|---|---|---|---|
| 6,757,006 | B1* | 6/2004 | Yabe | H04N 7/18 |
| | | | | 348/575 |
| 6,952,231 | B1* | 10/2005 | Paavola | G02B 13/22 |
| | | | | 348/142 |
| 2002/0038588 | A1* | 4/2002 | Newnes | B27B 1/007 |
| | | | | 83/75.5 |

FOREIGN PATENT DOCUMENTS

| | | |
|---|---|---|
| CA | 2494012 A1 | 1/2006 |
| CA | 2886801 A1 | 4/2014 |

* cited by examiner

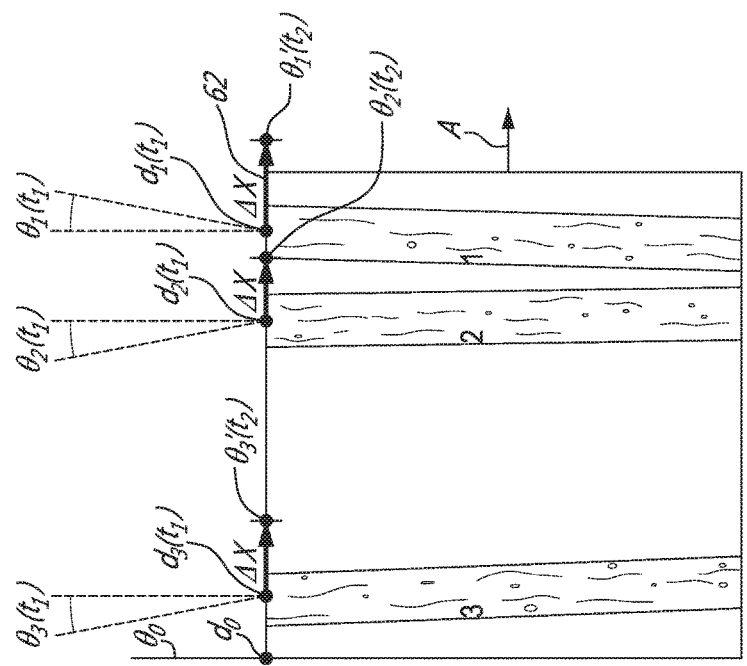
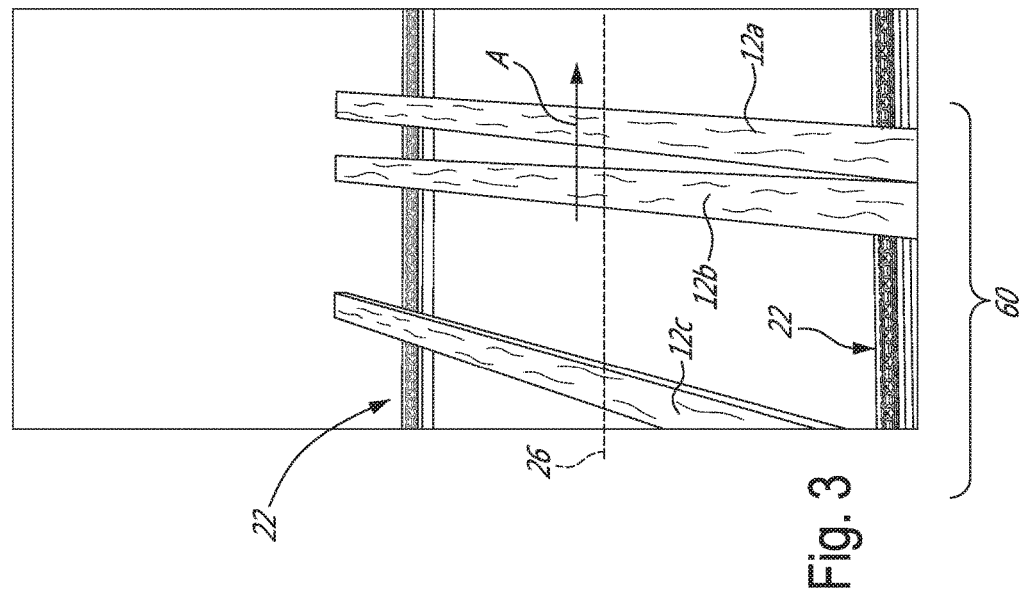

TRACKING SYSTEM AND METHOD FOR TRACKING WOOD PRODUCTS IN A PRODUCTION LINE

FIELD

The improvements generally relate to a wood product production line including an optimizer and a trimmer, and more particularly relates to a tracking system which helps tracking each wood product from the optimizer to the trimmer.

BACKGROUND

In the wood product industry, prices can vary on a daily basis. Accordingly, it is of importance for a wood product producer to optimize its production based on the current prices. More specifically, the pricing of the wood product can vary depending of its dimensions (e.g. length) and quality. Although greater length of wood products is typically associated with greater pricing, the presence of a defect along a length of the wood product can negatively affect the quality level of the product as a whole. Accordingly, in some instances, it is preferable to trim the defect off in a manner to obtain a shorter wood product of a greater quality, for instance.

Considering that, in a typical production line, the wood products are moved at a speed that can range between 366 m/min (1200 ft./min) and 610 m/min (2000 ft./min), these decisions have to be taken in an automated manner.

Accordingly, an example of a production line can include one or more conveyors for moving, for instance, wood products from a wood product optimizer to a wood product trimmer (simply referred to as "the optimizer" and "the trimmer"). The optimizer is generally configured to scan successive ones of the wood products, to decide whether or not and how to trim each wood product based on the current prices and to generate optimization data that the trimmer can use as cutting instructions on how to trim the wood product.

To ensure that given optimization data be used for a corresponding wood product, the typical production line generally includes a wood tracker. An example of such a wood tracker is provided in Canadian Patent Application No. 2 245 412 A1. For instance, this wood tracker applies an information mark pattern indicative of the optimization data on each wood product following scanning by the optimizer using upper and lower pairs of luminescent ink-jet devices. Prior to arriving to the trimmer, the wood tracker uses optical sensing devices each having luminescence inducing light source to read the information mark pattern and generates an output signal based on the reading of the optical sensing devices. The output signal is then used by the trimmer as cutting instructions to trim the wood product in accordance with its optimization data.

Although existing wood trackers were satisfactory to a certain degree, there always remains room for improvement.

SUMMARY

For instance, there is a specific need in avoiding the use of ink-jet devices, and any other marking device, in such a production line. For instance, maintenance of these marking devices has been found to be costly in terms of productivity because any time one of the marking devices breaks, the production line has to be stopped for a given period of time. In another example, the information mark pattern marked on a wood product happens to be applied onto a defect of the wood product which may later prevent readability of the information mark pattern. For at least these reasons, existing wood trackers have been found considerably impairing the productivity of the production line.

There is provided a wood tracking system using computer vision which can avoid the aforementioned drawbacks of the existing wood product trackers. By analyzing successive images of a handling area, each wood product can be tracked from the optimizer to the trimmer without marking directly on the wood product.

It is thus contemplated that an aim of the wood tracking system is to reduce costs associated to existing wood trackers (e.g., costs of luminescent ink, costs of ink-jet device parts, costs of the maintenance thereof, costs associated to the presence of unidentifiable wood product along the production line).

In accordance with another aspect, there is provided a wood tracking system for a production line, the wood tracking system comprising: a wood product optimizer positioned along a production line; a wood product trimmer positioned downstream from the wood product optimizer in the production line; a conveyor configured for moving a plurality of wood products from the wood product optimizer to the wood product trimmer and across a handling area between the wood product optimizer and the wood product trimmer, the wood product optimizer being configured to scan each of the wood products in a given order and to generate optimization data for each wood product; and a computer vision system positioned proximate the handling area along the production line, the computer vision system having a camera, a processor in communication with the wood product optimizer and with the wood product trimmer and a computer-readable memory for storing the optimization data, the processor being configured to acquire at least two images from the camera and representing the handling area at at least two different moments in time, the processor being configured to associate the optimization data of a given wood product represented in a first one of the at least two images to a corresponding wood product represented in a second one of the at least two images until the given wood product arrives at the trimmer.

In accordance with another aspect, there is provided a method of tracking wood products being transversely moved across a handling area of a production line at a transverse speed, the method comprising: obtaining position and orientation data and optimization data associated to each wood product of a first sample present in the handling area at a first moment in time; using a processor, anticipating position and orientation data of each wood product of the first sample at a second moment in time assuming an incremental transverse movement based on the transverse speed and on the position and orientation data associated to each wood product of the first sample; acquiring, from a camera, an image representing each wood product of a second sample present in at least the handling area at the second moment in time and analyzing the image to determine actual position and orientation data associated to each wood product of the second sample; and tracking each wood product from the first sample to the second sample by associating the optimization data of each wood product of the first sample to a respective wood product of the second sample based on the anticipated and actual position and orientation data.

In accordance with another aspect, there is provided a method wherein a step of obtaining position and orientation data associated to one or more wood products includes acquiring, from the camera, an image representing each wood product present in the handling area at a given moment in time; and analyzing the image to determine the position and orientation data associated to each wood product present in the handling area at the given moment in time.

Many further features and combinations thereof concerning the present improvements will appear to those skilled in the art following a reading of the instant disclosure.

DESCRIPTION OF THE FIGURES

In the figures,

FIG. 3 is an oblique view of a portion of the handling area of the production line of FIG. 1 at a first moment in time whereas FIG. 3A is a first image representing a portion of the handling area of FIG. 3;

FIG. 4 is an oblique view of a portion of the handling area of the production line of FIG. 1 at a second moment in time whereas FIG. 5 is an oblique view of a portion of the handling area of the production line of FIG. 1 at a third moment in time whereas

DETAILED DESCRIPTION

Figure 1:
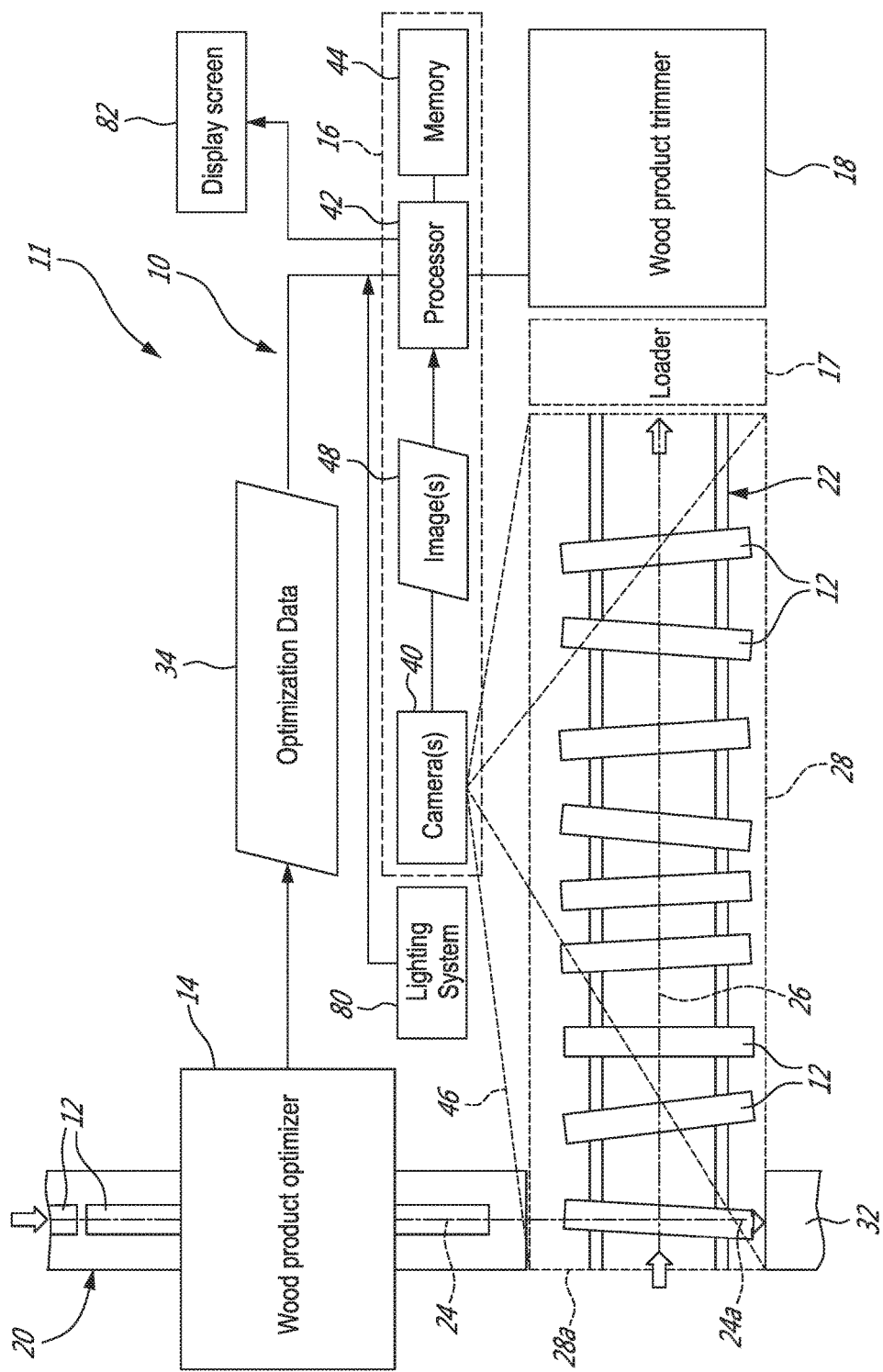
FIG. 1 is a schematic view of an example of a production line for wood products.

FIG. 1 shows an example of a wood tracking system 10 of a production line 11 for elongated wood products 12 such as lumbers, logs and the like (simply referred to as "wood products 12").

As depicted, the wood tracking system 10 includes an optimizer 14, a computer vision system 16 and a trimmer 18. An optional wood product loader 17 may be provided upstream from the trimmer 18 and proximate thereto to load each wood product into the trimmer 18.

In this example, the movement of the wood products 12 is allowed by two separate conveyors, one being a longitudinal conveyor 20 and the other being a transverse conveyor 22. It is understood that in other embodiments, the number, type and arrangement of conveyor(s) may differ.

For instance, the longitudinal conveyor 20 is used to move the wood products 12 along a longitudinal path 24 and across an optimization area proximate to the optimizer 14. The transverse conveyor 22 is used to move the wood products 12 from an end 24a of the longitudinal path 24, along a transverse path 26 at a transverse speed, across a handling area 28 of the production line and towards a downstream cutting area proximate to the trimmer. Handling of the wood products for manual and visual inspection may be limited to the handling area 28.

Since longitudinal speeds involved in such a production line 11 are relatively fast (e.g., between 366 m/min and 610 m/min), a stopper 32 can be provided proximate to the end 24a of the longitudinal path 24 to stop each wood product 12 as they are "thrown" by the longitudinal conveyor 20 towards the stopper 32.

The optimizer 14 is configured to scan successive ones of the wood products 12 and to generate optimization data 34 for each wood product 12. In this example, the optimization data 34 are sequentially transmitted to the trimmer 18 in a particular order such that a queue of optimization data arrives at the trimmer 18 during use. The optimization data can include identification data indicating an order number of a given wood product in the queue, a type of the given wood product, a grade of the given wood product, a price, etc.

It is thus understood that any reordering of the wood products 12 between the optimizer 14 and the trimmer 18 may lead to a wood product being trimmed using the optimization data of another wood product and cause inefficiencies in the production line 11. For instance, some wood products may be reordered from their given order following unexpected bouncing onto the stopper 32. Some other wood products may be reordered by handling of the wood products in the handling area 28. Other reasons for reordering may also apply.

To address potential reordering of the wood product 12, the computer vision system 16 of the wood tracking system 10 can be used to track each wood product 12 in the handling area 28 such that any reordering of the wood product 12 causes reordering of the optimization data in order for the trimmer 18 to trim each wood product 12 with their corresponding optimization data.

More specifically, the computer vision system 16 has a camera 40, a processor 42 in communication with the optimizer 14 and with the trimmer 18 and a computer-readable memory 44.

More specifically, the camera 40 has a field of view 46 substantially corresponding to the handling area 28. The handling area 28 can extend from the end 24a of the longitudinal path 24 of the longitudinal conveyor 20 to an end 26a of the transverse path 26 of the transverse conveyor 22.

The camera 40 is configured to generate one or more images 48 representing the handling area 28 at each of successive moments in time during use of the wood tracking system 16. In this embodiment, the camera 40 has a frame rate of at least 20 fps and has a resolution of at least 1 megapixel. The frame rate of the camera, as well as its shutter speed, can be controlled by the processor 42, for instance. It is noted that depending on the application, the camera 40 can be configured to generate 2D images and/or 3D images. As it will be understood, in an alternate embodiment, the camera 40 includes more than one camera unit such that the field of view 46 is composite (i.e. the field of view results from the combination of more than one field of view of corresponding camera units). For ease of reading, however, the term "camera" is used in its singular form.

As shown in FIG. 1, the processor 42 is connected to the optimizer 14, to the camera 40 and to the trimmer 18 in a wired and/or wireless fashion. In this embodiment, the processor 42 is configured to receive the optimization data 34 from the optimizer 14, to acquire the images 48 from the camera 40 and to transmit the optimization data 34 to the trimmer 18 in an order corresponding to the actual order the wood products 12 arriving to the trimmer 18. The processor 42 can include one or more processors but the term "processor" is used in its singular form for ease of reading. In an alternate embodiment, the processor 42 is remote from the production line 11.

In the example shown in FIG. 1, the processor 42 is in communication with the memory 44. The processor 42 and the memory 44 can be part of a computer (e.g., a personal computer, mobile device, etc.). In this embodiment, the memory 44 has stored thereon a wood tracking program, which, when run by the processor 42, allows the wood tracking system 16 to track the optimization data 34 of each wood product 12 across a plurality of images 48 representing the handling area 28 such that, when a given wood product 12 arrives at the trimmer 18, the processor 42 can transmit corresponding optimization data 34 for proper cutting.

The instructions of the wood tracking program can be presented in the form of steps of a method that are to be performed by the processor 42.

Figure 2:
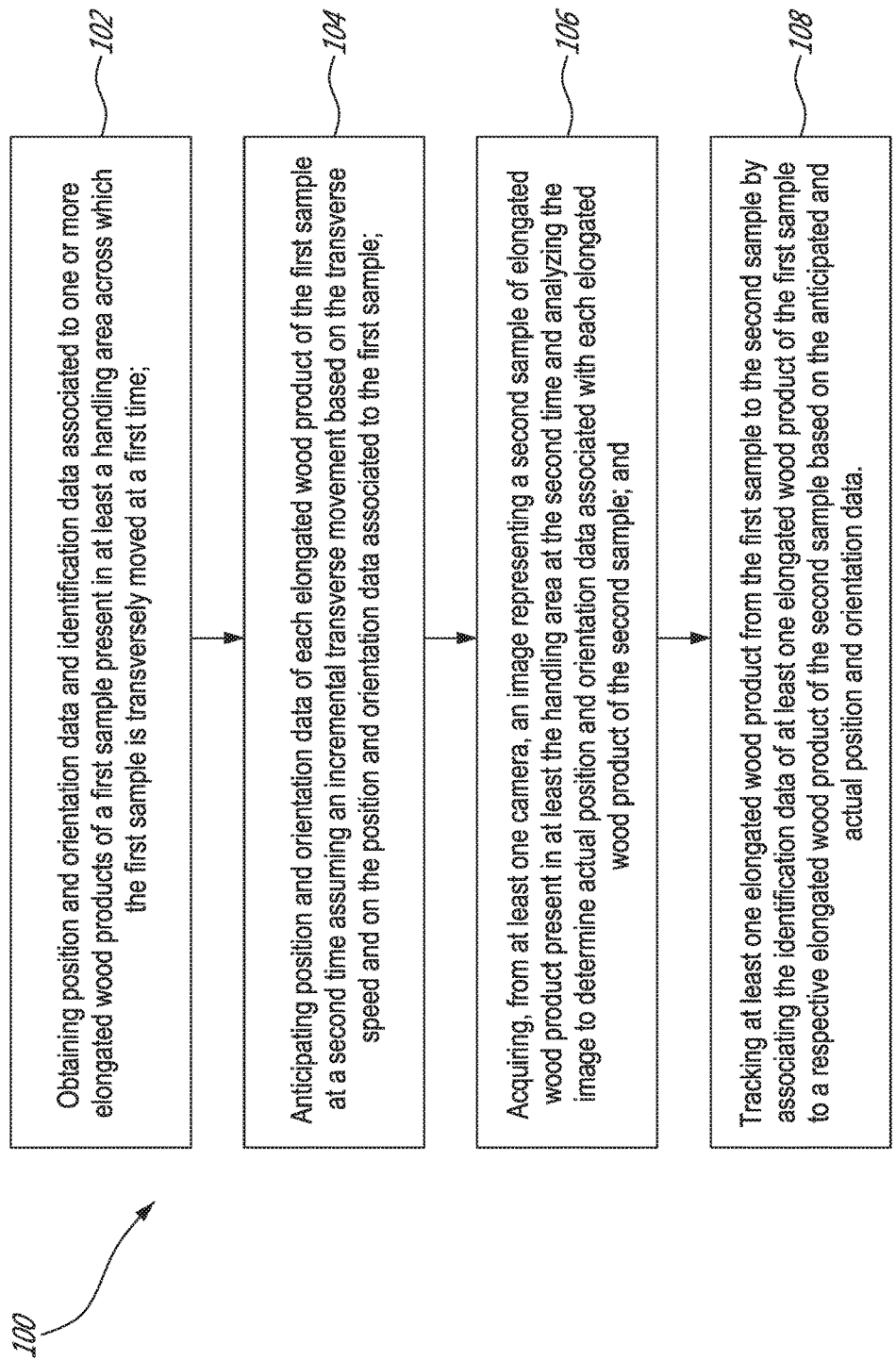
FIG. 2 is a flowchart of an example of a method of tracking wood products being transversely moved across a handling area of the production line of FIG. 1.

For instance, FIG. 2 shows an example of a method 100 of tracking wood products that are transversely moved across the handling area of the production line at a transverse speed.

As shown, the method 100 has a step 102 of obtaining position and orientation data as well as optimization data associated to each wood product of a first sample present in the handling area at a first moment in time t1.

Referring now to FIGS. 3 and 3A, each position and orientation data are indicative of a position and of an orientation ($\theta$,d) of a given wood product relative to a reference coordinate system (e.g., the reference system $\theta 0$,d0). Each image of the handling area is calibrated based on the reference coordinate system to allow comparison between successive images.

It will be understood that in such a production line, each wood product is a wood product and can be modeled as being a line having a given position relative to a reference point d0 (e.g., the upper left corner of the image) and extending along a given orientation $\theta 0$ relative to a reference orientation (e.g., the vertical orientation).

For ease of understanding, reference is now made to FIG. 3 which shows an oblique view of a first sample 60 in a handling area at a first moment in time t1 where a first wood product 12a, a second wood product 12b and a third wood product 12c are being transversally moved along the transverse path 26 by the transverse conveyor 22. FIG. 3A shows an example of a first image 62 generated by the camera at the first moment in time t1. A direction of transverse movement is shown at arrow A in FIGS. 3 and 3A.

As it will be understood, the position and orientation data can be obtained from the memory where those data have been previously stored. In this embodiment, however, the position and orientation data associated to each of the first, second, and third wood products 12a,12b,12c of the first sample 60 are obtained by analyzing the first image 62 acquired from the camera.

As it can be seen, the first image 62 can be analyzed by the processor to determine first position and orientation data indicative of the actual position and the orientation ($\theta 1$(t1), d1(t1)) associated to the first wood product 12a at the first moment in time t1, to determine second position and orientation data indicative of the actual position and the orientation ($\theta 2$(t1),d2(t1)) associated to the second wood product 12b at the first moment in time t1, and to determine third position and orientation data indicative of the actual position and the orientation ($\theta 3$(t1),d3(t1)) associated to the third wood product 12c at the first moment in time t1. In this case, first optimization data are associated to the first wood product 12a, second optimization data are associated to the second wood product 12b and third optimization data are associated to the third wood product 12c.

At this stage, referring back to FIG. 2, the method 100 has a step 104 of anticipating position and orientation data indicative of the position and of the orientation ($\theta'$(t2),d'(t2)) of each wood product of the first sample but at a second moment in time t2 assuming an incremental transverse movement $\Delta x$ based on the transverse speed and on the position and orientation data associated to the first, second and third wood product 12a,12b,12c of the first sample 60. The incremental transverse movement $\Delta x$ is assumed to last for an incremental period of time $\Delta t$ such that the second moment in time t2 exceeds the first moment in time t1 by the incremental period of time $\Delta t$ (i.e. t2=t1+$\Delta t$).

As will be understood, if no reordering occurs between the first and the second moments in time t1 and t2, the anticipated orientation of a wood product at the second moment in time t2 can correspond to the actual orientation of the same wood product at the first t1 (i.e., $\theta'$(t2)=$\theta$(t1)) whereas the anticipated position of a wood product at the second moment in time t2 can correspond to the actual position of the same wood product at the first moment in time t1 plus the incremental transverse movement $\Delta x$ (i.e., d'(t2)=d(t1)+$\Delta x$).

For instance, anticipated position and orientation data associated to the first wood product, the second wood product and the third wood product ($\theta 1'$(t2),d1'(t2)), ($\theta 2'$(t2),d2'(t2)) and ($\theta 3'$(t2),d3'(t2)) are shown in the first image 62 of FIG. 3A.

Referring back to FIG. 2, the method 100 has a step 106 of acquiring, from the camera, a second image representing each wood product of a second sample present in the handling area at the second moment in time t2.

Figure 4A:
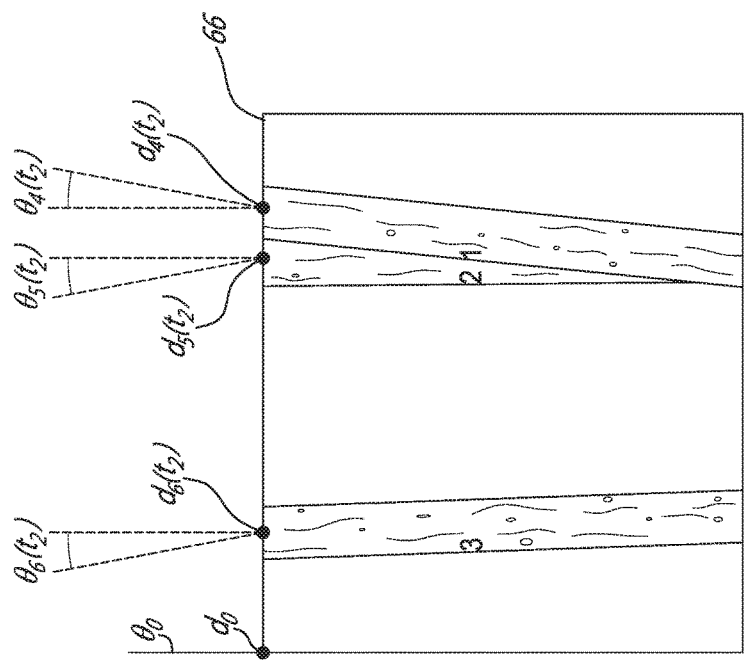
FIG. 4A is a second image representing a portion of the handling area of FIG. 4.
Figure 4:
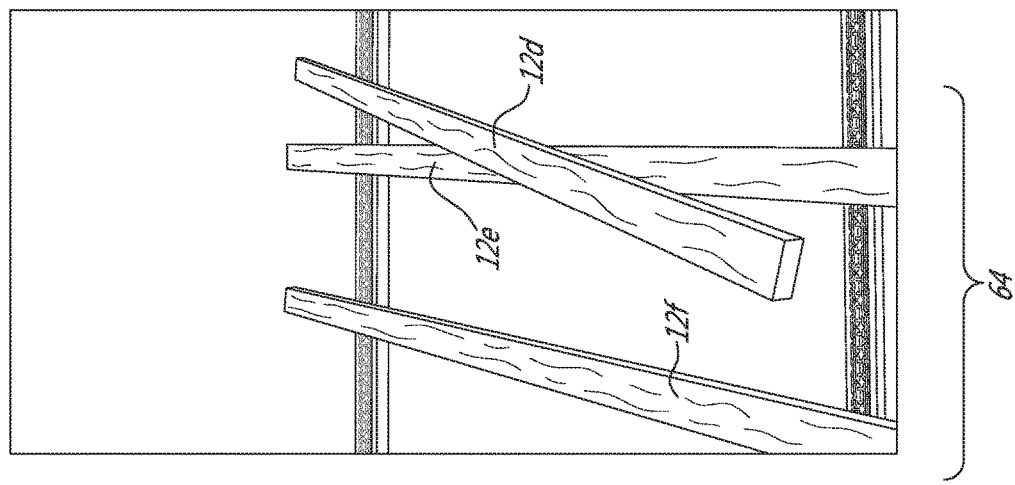

Referring now to FIG. 4, fourth, fifth and sixth wood products 12d,12e,12f of a second sample 64 are in the handling area at a second moment in time t2. The fourth, fifth and sixth wood products 12d,12e,12f may correspond to a respective one of the first, second and third wood products 12a,12b,12c, however, the correspondence is not assumed to be known in order to account for potential reordering.

In other words, in this case, the first, second and third wood products 12a,12b,12c of the first sample 60 can be said to be wood products identified in a previous image whereas the fourth, fifth and sixth wood products 12d,12e,12f of the second sample 64 can be said to be wood products identified in a later image. The method described herein helps associate each wood product identified in a previous image to a wood product identified in a later image.

FIG. 4A shows a second image 66 of the second sample 64. The second image 66 can thus be analyzed to determine actual position and orientation data ($\theta$(t2),d(t2)) associated to the fourth, fifth and sixth wood products 12d,12e,12f of the second sample 64 at the second moment in time t2.

As it can be seen from FIGS. 4 and 4A, the second image 66 can be analyzed by the processor to determine fourth position and orientation data indicative of the position and the orientation ($\theta 4$(t2),d4(t2)) associated to the fourth wood product 12d at the second moment in time t2, to determine fifth position and orientation data indicative of the position and the orientation ($\theta 5$(t2),d5(t2)) associated to the fifth wood product 12e at the second moment in time t2, and to determine sixth position and orientation data indicative of the position and the orientation ($\theta 6$(t2),d6(t2)) associated to the sixth wood product 12f at the second moment in time t2.

For now, the optimization data associated to each of the fourth, fifth and sixth wood products 12d,12e,12f are still unknown.

At this stage, referring back to FIG. 2, the method 100 has a step 108 of tracking each wood product from the first sample at the first moment in time t1 to the second sample at the second moment in time t2 by associating the optimization data of each wood product of the first sample to a respective wood product of the second sample based on the anticipated and actual position and orientation data ($\theta'$(t2), d'(t2)) and ($\theta$(t2),d(t2)).

Indeed, in an exemplary embodiment, the method 100 can have a step of calculating a distance parameter between all combinations of the anticipated and actual position and orientation data such that the step of associating is based on the calculated distance parameters.

The calculus of the distance parameter can vary from an embodiment to another. For instance, the following matrix shows exemplary distance parameters associated to each of all combinations between the anticipated and actual position and orientation data of the first and second samples 60 and 64 of FIGS. 3A and 4A:

|  | (θ'1(t2), d'1(t2)) | (θ'2(t2), d'2(t2)) | (θ'3(t2), d'3(t2)) |
|---|---|---|---|
| (θ4(t2), d4(t2)) | 29 | 189 | 353 |
| (θ5(t2), d5(t2)) | 166 | 34 | 168 |
| (θ6(t2), d6(t2)) | 287 | 143 | 57 |

In one embodiment, the step of tracking can be performed by associating each combination characterized by a calculated distance parameter smaller than a distance parameter threshold.

In this case, assuming that the distance parameter threshold is 142, the combinations (θ'1(t2),d'1(t2))-(θ'1(t2),d'1(t2)), (θ'2(t2),d'2(t2))-(θ5(t2),d5(t2)) and (θ'3(t2),d'3(t2))-(θ6(t2),d6(t2)) are retained, which can be used to associate the first optimization data of the first wood product to the fourth wood product, to associate the second optimization data of the second wood product to the fifth wood product and to associate the third optimization data of the third wood product to the sixth wood product.

It is contemplated that if an object in the second image remains unassociated to corresponding optimization data, this object can be considered as a new wood product if i) it arrives from an incoming side of the handling area (e.g., from incoming side 28a of the handing area 28 of FIG. 1); and ii) if new optimization data have been received by the optimizer. Moreover, if optimization data associated with a given wood product found in a first image but not found in a second or subsequent images, these optimization data can be removed from further consideration (e.g., the given wood product can be assumed to be removed from the handling area).

In another embodiment, the step of tracking can be performed by determining which of the combinations has a minimized distance parameter and associate optimization data of a given wood product of the first sample associated to the anticipated position and orientation data of the determined combination to a given wood product of the second sample associated to the actual position and orientation data of the determined combination. Once this association is performed, the previously associated wood products can be removed from further consideration so that this step of associating can be performed iteratively until there is no longer optimization data remain to associate.

For instance, using the exemplary matrix shown above, the combination which yields a minimized distance parameter is the combination (θ'2(t2),d'2(t2))-(θ5(t2),d5(t2)). In this case, the optimization data of the second wood product are associated to the fifth wood product and the second and fifth product are removed from further consideration.

Following removal from consideration the combinations involving the second wood product and the fifth wood product, the matrix becomes:

|  | (θ'1(t2), d'1(t2)) | (θ'3(t2), d'3(t2)) |
|---|---|---|
| (θ4(t2), d4(t2)) | 29 | 353 |
| (θ6(t2), d6(t2)) | 287 | 57 |

Now, the combination which yields a minimized distance parameter is the combination (θ'3(t2),d'3(t2))-(θ6(t2),d6(t2)). In this case, the optimization data of the third wood product are associated to the sixth wood product.

Following removal from consideration the combinations involving the third wood product and the sixth wood product, there only remains the optimization data associated to the first wood product to associate, and there only remains the fourth wood product to which it can be associated. Therefore, the optimization data associated to the first wood product are associated to the fourth wood product.

By so tracking the optimization data relative to its associated wood product across successive ones of a plurality of images representing the handling area, the processor of the wood tracking system can transmit the optimization data that corresponds to the wood product that is to be trimmed by the trimmer.

Figure 5A:
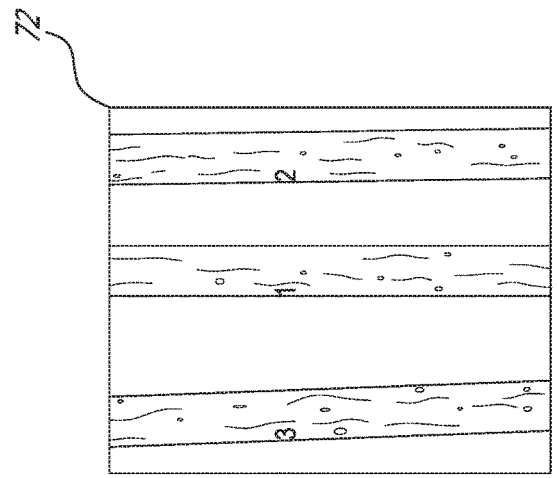
FIG. 5A is a third image representing a portion of the handling area of FIG. 5.
Figure 5:
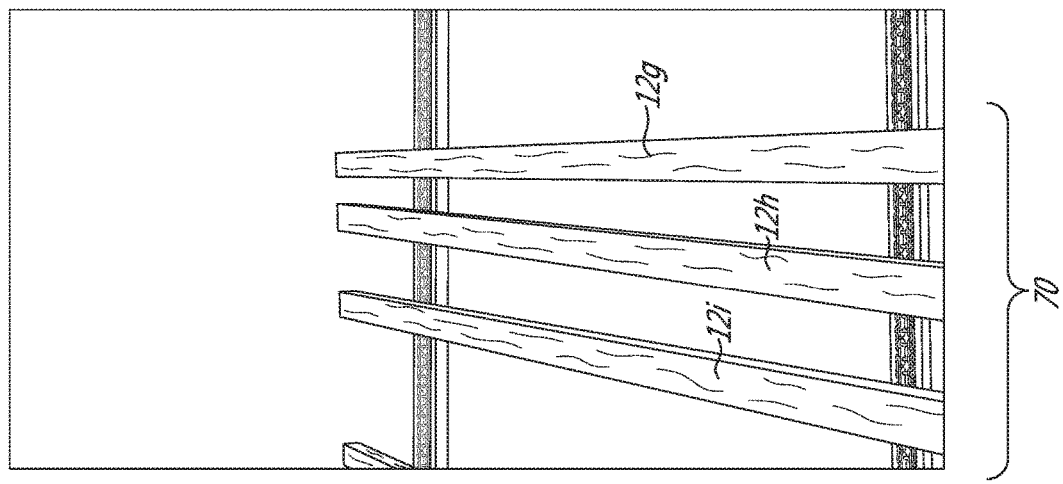

For instance, as it can be seen in FIG. 5, seventh, eighth, and ninth wood products 12g,12h,12i of a third sample 70 are shown at a third moment in time t3. A third image 72 representing the third sample 70 is presented in FIG. 5A. However, by repeatedly performing the steps of the method 100 described with reference to FIG. 2 on the third image 72 as shown especially in FIG. 5A, these wood products 12g,12h,12i can be associated respectively to the first, second and third wood products 12a,12b,12c.

Indeed, the first and second wood products 12a,12b have been reordered along the transverse path between the second moment in time t2 and the third moment in time t3.

In this case, the processor can transmit the optimization data associated to the second wood product to the trimmer, then the optimization data associated to the first wood product and then the optimization data associated to the third wood product.

For the wood tracking system to work in a satisfactory manner, the repetition rate of these steps can be above a given threshold. The incremental period of time Δt between the first, second and third images 62, 66 and 72 is about a fraction of a second. In another embodiment, the incremental period of time Δt between two successive repetition of the method is at least 0.05 s (i.e. 20 fps).

As it will be understood, there are various ways of modeling each wood product in an image. The following presents one exemplary method of doing so.

The step of comparing can includes a step of convoluting the image with a convolution matrix (e.g., [+1|−1]) to obtain a convoluted image.

The step of modeling can include a step of thresholding the image (e.g., the convoluted image) to obtain a binary image.

The step of modeling can include a step of applying a Hough transform to the binary image, wherein the position and orientation data and the distance parameters are determined from a parameter space of the Hough transform. An example of a Hough transform is presented in U.S. Pat. No. 3,069,654, the contents of which are incorporated by reference herein.

Referring back to FIG. 1, the wood tracking system 10 has a lighting system 80 for lighting the handling area 28 during use of the wood tracking system 10. As shown in the illustrated example, the lighting system 80 is controllable by the processor 42 to provide a controlled lighting environment to the handling area 28. For instance, the processor 42 can transmit a control signal to the lighting system 80 in order to modify the lighting of the handling area 28 based on the images 48 acquired from the camera 40. However, the lighting system 80 of the wood tracking system 10 is optional. Indeed, in some embodiments, the handling area 28 is illuminated by a conventional lighting system of a facility in which the wood tracking system 10 is used. In some other embodiments, natural illumination (e.g., sunlight) of the handling area 28 may be sufficient to allow the camera 40 to generate satisfactory images in at least some cases. The camera 40 can have a sensibility which compensates for a poor illumination of the handling area 28.

It is envisaged that the wood tracking system 10 can include a display screen 82 in communication with the processor 42 and located a position along the production line 11. The display screen 82 can be used to display the acquired images 48 in the form of a real-time video and also optionally to display optimization data 34 for each wood product 12 such as to allow validation of the optimization data 34 by a skilled operator. This can allow to reduce time associated with a validation procedure of the optimization data to ensure that the optimizer 14 works in a satisfactory manner in the production line 11. For instance, it may be possible to validate the optimization data of 20 wood products in less than 5 minutes.

In an embodiment, the optimization data associated to a given one of the wood products are displayed on the display screen 82 when the wood tracking system 10 determines, in an image, that a skilled operator is pointing or touching the given wood product in the handling area 28.

As can be understood, the examples described above and illustrated are intended to be exemplary only. In an embodiment, the trimmer can be provided in the form of an edger. Moreover, in another embodiment, the conveyor associated with the optimizer can be a transversal conveyor. In such an embodiment, the wood products may be tied to one another as they pass under the optimizer and then be freed from one another prior to arrival in the handling area. The scope is indicated by the appended claims.

What is claimed is:

1. A wood tracking system for a production line, the wood tracking system comprising:
   a wood product optimizer positioned along a production line;
   a wood product trimmer positioned downstream from the wood product optimizer in the production line;
   a conveyor configured for moving a plurality of wood products from the wood product optimizer to the wood product trimmer and across a handling area between the wood product optimizer and the wood product trimmer, the wood product optimizer being configured to scan each of the wood products in a given order and to generate optimization data for each wood product; and
   a computer vision system positioned proximate the handling area along the production line, the computer vision system having a camera, a processor in communication with the wood product optimizer and with the wood product trimmer and a non-transitory computer-readable memory for storing the optimization data, the processor being configured to acquire at least two images from the camera and representing the handling area at, at least two different moments in time, the processor being configured to associate the optimization data of a given wood product represented in a first one of the at least two images to a corresponding wood product represented in a second one of the at least two images until the given wood product arrives at the trimmer;
   the non-transitory computer-readable memory having stored thereon instructions that, when executed by the processor, perform the steps of:
   determining position and orientation data associated to each wood product represented in each of the at least two images; and
   associating the optimization data of each wood product represented in the first image to a respective wood product represented in the second image based on the position and orientation data determined in the first and second images.

2. The wood tracking system of claim 1 further comprising a lighting system in communication with the processor to control a lighting environment of the handling area.

3. The wood tracking system of claim 1 wherein the camera includes more than one cameras each having a corresponding field of view associated to a given sub portion of the handling area.

4. The wood tracking system of claim 1 wherein the camera has a frame rate of at least 20 fps.

5. The wood tracking system of claim 1 wherein the camera has a resolution of at least 1 megapixel.

* * * * *